US010251609B2

(12) United States Patent
Koyama et al.

(10) Patent No.: US 10,251,609 B2
(45) Date of Patent: Apr. 9, 2019

(54) BODY WATER METER AND TERMINAL

(71) Applicant: TERUMO KABUSHIKI KAISHA, Tokyo (JP)

(72) Inventors: Miyuki Koyama, Kanagawa (JP); Kei Honda, Kanagawa (JP); Yuusuke Sekine, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 702 days.

(21) Appl. No.: 14/819,564

(22) Filed: Aug. 6, 2015

(65) Prior Publication Data
US 2016/0073968 A1 Mar. 17, 2016

Related U.S. Application Data

(63) Continuation of application No. PCT/JP2013/000897, filed on Feb. 19, 2013.

(51) Int. Cl.
*A61B 5/00* (2006.01)
*A61B 5/053* (2006.01)
*A61B 5/01* (2006.01)

(52) U.S. Cl.
CPC .......... *A61B 5/7246* (2013.01); *A61B 5/0004* (2013.01); *A61B 5/0008* (2013.01);
(Continued)

(58) Field of Classification Search
CPC ....... A61B 5/0004; A61B 5/0008; A61B 5/01; A61B 5/0537; A61B 5/4875; A61B 5/7246; A61B 5/7271; A61B 5/742; A61B 5/746
See application file for complete search history.

(56) References Cited

U.S. PATENT DOCUMENTS

2002/0022786 A1 2/2002 Takehara et al.
2005/0228242 A1 10/2005 Kawamura et al.
(Continued)

FOREIGN PATENT DOCUMENTS

JP 2000-166881 6/2000
JP 2002-034946 2/2002
(Continued)

OTHER PUBLICATIONS

International Search Report with English translation for International (PCT) Patent Application No. PCT/JP2013/000897 dated May 28, 2013, 5 pages.
(Continued)

*Primary Examiner* — Boniface Nganga
(74) *Attorney, Agent, or Firm* — Jason H. Vick; Sheridan Ross, PC

(57) ABSTRACT

Devices and systems are provided to determine the condition of a subject comprehensively on the basis of a measurement result of a body water meter. The body water meter measures the amount of water in a subject's body and includes direction means and output means. The direction means, when water amount data is acquired through the measurement of the amount of water, directs a server that manages data regarding living body information on the subject to search for another piece of data acquired through measurement of living body information on the subject other than the amount of water and that satisfies a predetermined measurement condition. The output means outputs a message indicating the condition of the subject which is determined on the basis of the water amount data and the other piece of data on the subject received in response to the direction from the direction means.

20 Claims, 12 Drawing Sheets

(52) U.S. Cl.
CPC .............. *A61B 5/01* (2013.01); *A61B 5/0537* (2013.01); *A61B 5/4875* (2013.01); *A61B 5/7271* (2013.01); *A61B 5/742* (2013.01); *A61B 5/746* (2013.01)

(56) References Cited

U.S. PATENT DOCUMENTS

| | | | |
|---|---|---|---|
| 2008/0039700 A1* | 2/2008 | Drinan ................ | A61B 5/0537 600/301 |
| 2014/0018641 A1 | 1/2014 | Yoshino et al. | |
| 2014/0129252 A1 | 5/2014 | Inoue et al. | |

FOREIGN PATENT DOCUMENTS

| | | |
|---|---|---|
| JP | 2005-0319283 | 11/2005 |
| JP | 2012-176120 | 9/2012 |
| WO | WO2012/042878 | 4/2012 |
| WO | WO 2012/124330 | 9/2012 |
| WO | WO 2013/008554 | 1/2013 |

OTHER PUBLICATIONS

Official Action (with English translation) for Chinese Patent Applciation No. 201380070659.8, undated, 18 pages.
Written Opinion for International Application No. PCT/JP2013/000897, dated May 28, 2013.
International Preliminary Report on Patentability for International Application No. PCT/JP2013/000897, dated Sep. 3, 2015.

* cited by examiner

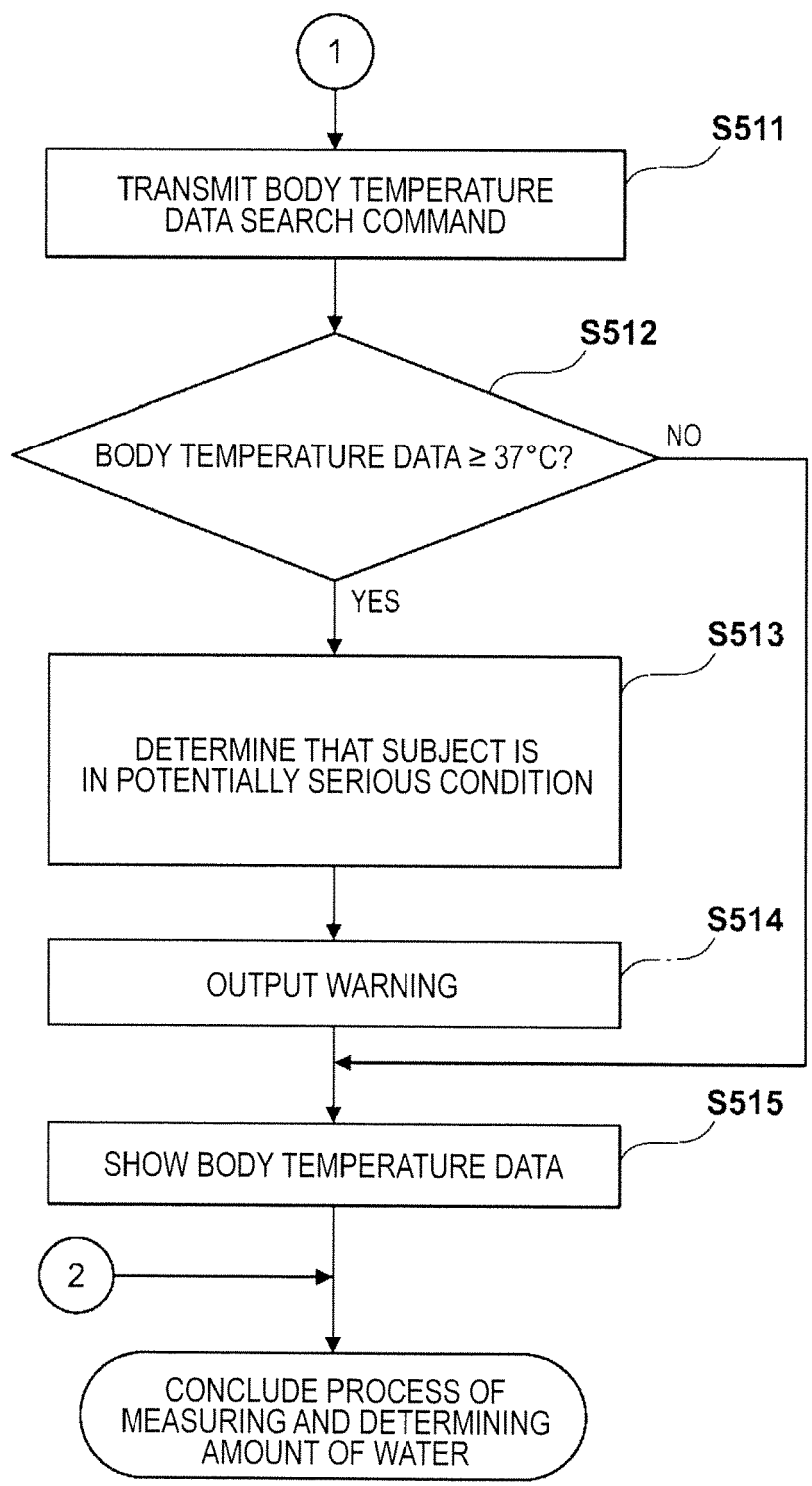

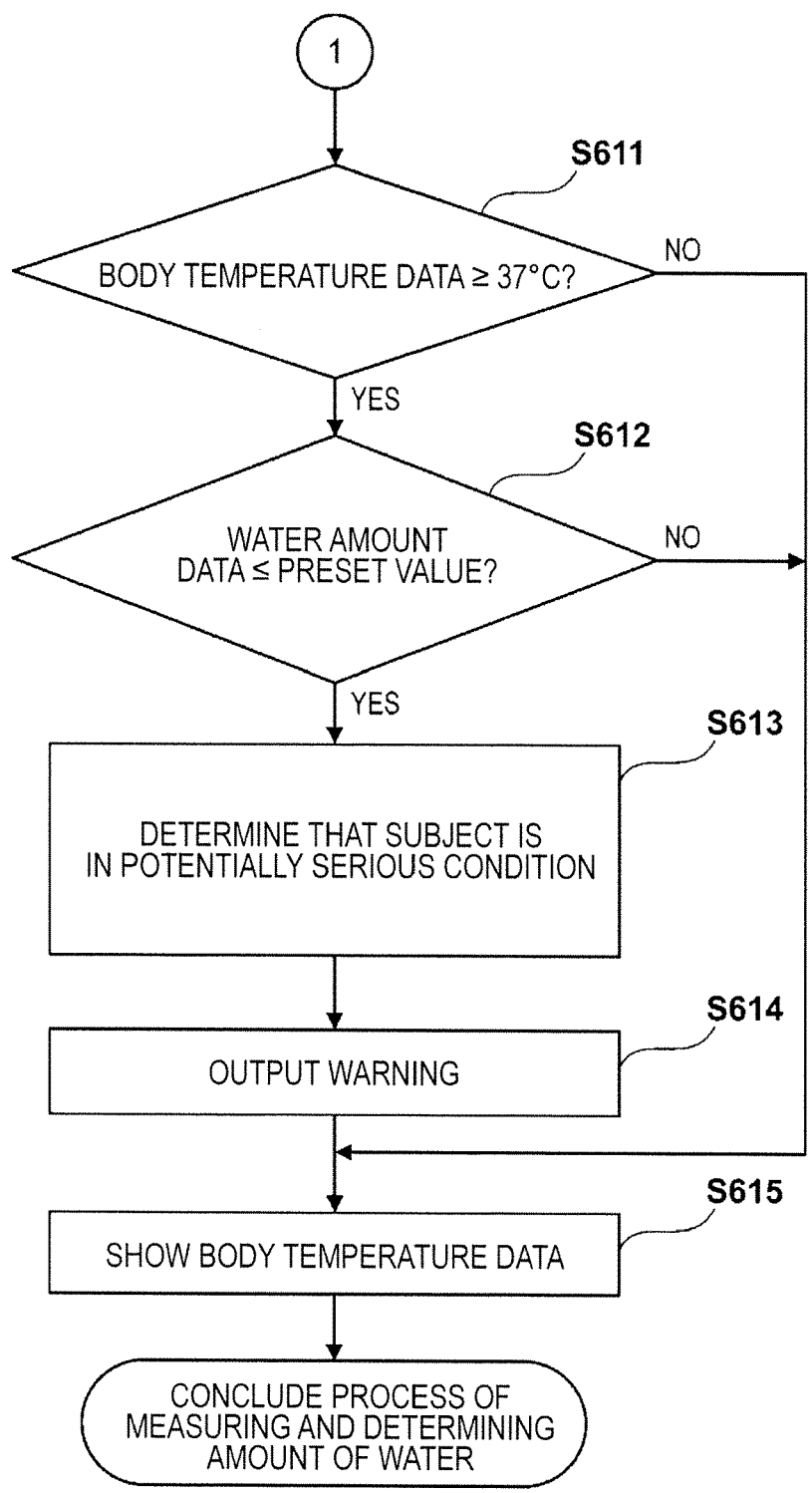

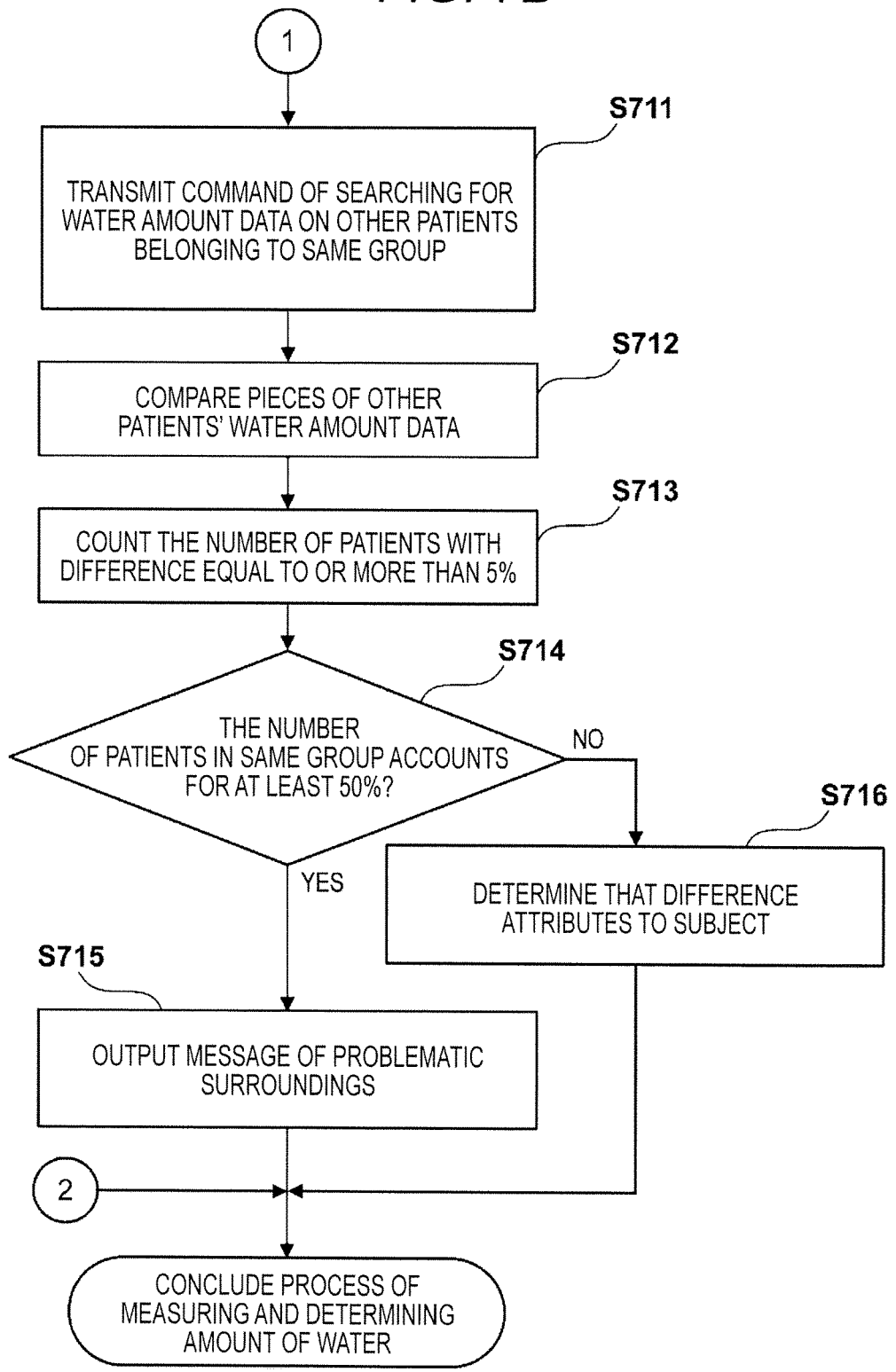

BODY WATER METER AND TERMINAL

CROSS REFERENCE TO RELATED APPLICATIONS

This application is a continuation of and claims priority to PCT/JP2013/000897, filed Feb. 19, 2013, entitled "Body Water Meter, and Terminal", which is incorporated herein by reference in its entirety, for all purposes, and for all that it teaches.

TECHNICAL FIELD

The embodiments described herein generally relate to devices for measuring the amount of water in a subject's body and a terminal that wirelessly communicates with a body water meter.

BACKGROUND

Measuring the amount of water in a subject's body is essential. Dehydration in a living body is a pathological condition in which water is reduced and often occurs when a person is exercising or when the temperature is high because a lot of water is excreted from the body by sweating to reduce an elevated body temperature.

Generally, when water, in a living body, is reduced by 3% or more of the body weight, body temperature regulation is disturbed. This disturbance of body temperature regulation causes the body temperature to increase, and then water in the living body is further reduced. In other words, a vicious cycle of dehydration is created, which leads to, at last, a pathological condition called heat illness. Heat illness includes conditions such as heat cramp, heat exhaustion, and heatstroke. In some cases, all the organs in the body are affected by heat illness.

Inpatients in hospitals and elderly persons in, for example, nursing homes tend to suffer from dehydration more seriously than healthy persons and non-elderly persons because most of them have lower capacities to regulate the body temperature. For that reason, for example, nurses in medical facilities such as hospitals and care persons in elder care facilities, such as, nursing homes need to regularly check and manage the amounts of body water in inpatients and elderly persons.

SUMMARY

Technical Problem

There are cases where measurers, including nurses and care persons, who have measured the amounts of body water in inpatients and elderly persons with body water meters can not make immediately a judgment on the severity of risks based on the measurement results.

As described above, the decrease in the amount of water in a subject's body is related closely to the capacity to regulate the body temperature. Measurers thus need to make a judgment on a severity of the risk based comprehensively on a decrease of the amount of body water and other pieces of living body information.

Moreover, after having assessed the decrease in the water in a subject's body from measurement results, a measurer, such as a nurse or a care person, still needs to determine whether it is ascribable to the subject himself/herself or the surroundings. A typical body water meter for measuring the amount of water in a subject's body simply provides a measurer with a current measurement result, but the measurer needs to know the amount of water in a subject's body in a normal condition to make comprehensive determination.

The embodiments described herein address the above disadvantages with an objective of determining the condition of a subject comprehensively on the basis of a measurement result of a body water meter.

Solution to the Problem

To achieve the above objective, embodiments of a body water meter provide a configuration described below.

The body water meter, which measures an amount of water in a subject's body, includes direction means and output means. The direction means, when the data of amount of water is acquired through measurement of the amount of water in the subject's body, directs a server that manages data regarding pieces of living body information on the subject to search for another piece of data acquired through measurement of one of the pieces of living body information on the subject other than the amount of water, the other piece of data satisfying a predetermined measurement condition. The output means outputs a message indicating a condition of the subject which is determined on the basis of both the water amount data and the other piece of data on the subject, which has been received in response to the direction from the direction means.

Advantageous Effects

The embodiments make it possible to determine the condition of a subject comprehensively on the basis of a measurement result of the body water meter.

The other features and advantages of the embodiments will become apparent from the following description with reference to the accompanying drawings. The same reference numerals are given to identical or similar constituent elements in the drawings.

BRIEF DESCRIPTION OF DRAWINGS

The accompanying drawings that are included in the description and constitute a part of the description illustrate the embodiments described herein, and are used to explain the features of the embodiments together with the description provided herein.

FIG. 5B is a flowchart of the processing through which the body water meter 100 measures and determines the amount of water in a patient's body.

FIG. 6B is a flowchart of the processing through which the body water meter 100 measures and determines the amount of water in a patient's body.

FIG. 7B is a flowchart of the processing through which the body water meter 100 measures and determines the amount of water in a patient's body.

DESCRIPTION

Some embodiments will be explained below with reference to the accompanying drawings. The embodiments described below are examples and thus undergo various technical limitations. The scope of the embodiments is, however, not limited to these embodiments unless there is any description being limited in the following explanation.

1. Exterior Configuration of Body Water Meter

Figure 1:
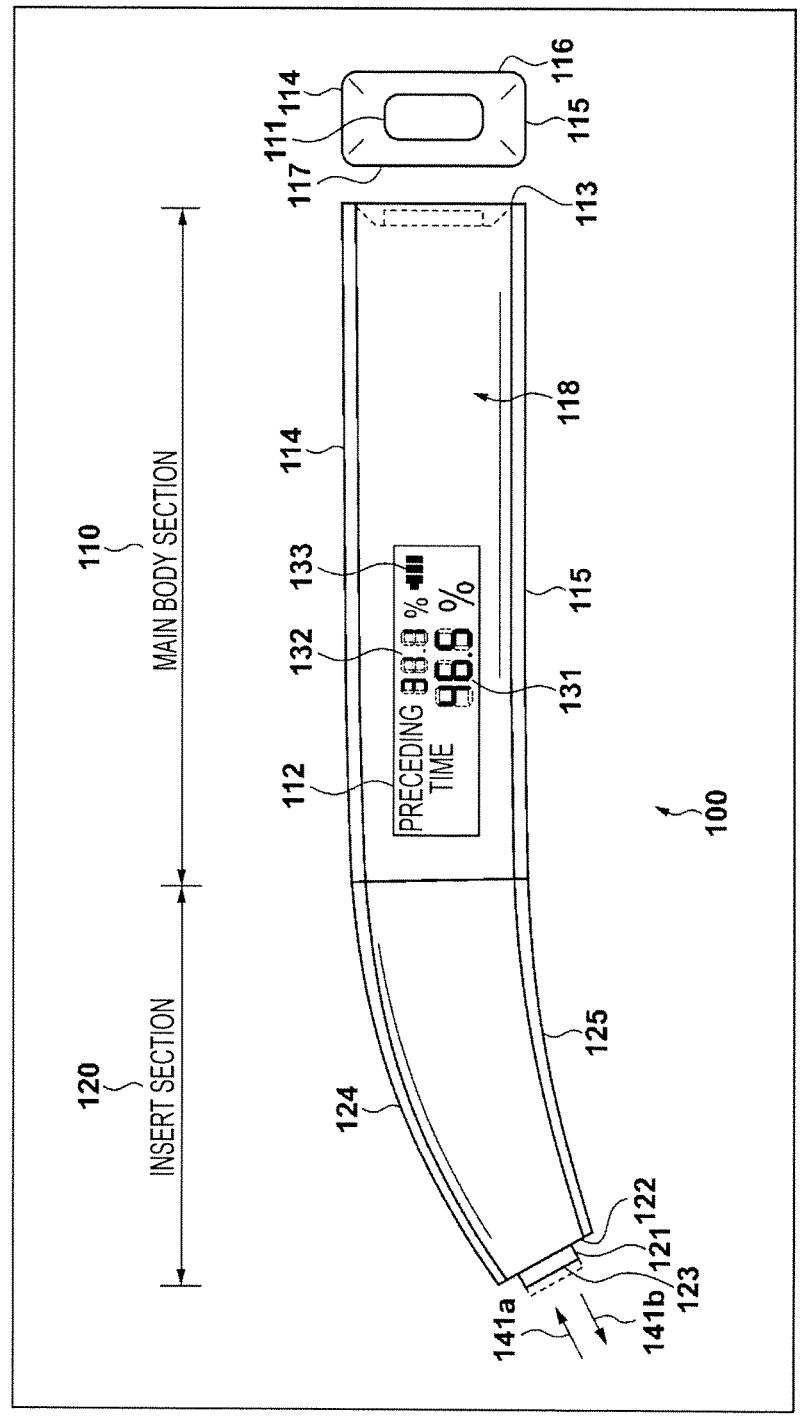
FIG. 1 is a view illustrating an embodiment of the exterior configuration of the body water meter 100.

FIG. 1 is a view illustrating an exemplary exterior configuration of a body water meter 100. The body water meter 100 detects the amount of water in the subject's body by supplying an electrical signal to a sensor 121 that is in contact with the armpit skin, or the outer surface, of a subject and senses a physical characteristic according to the electrical signal from the sensor 121. More specifically, the body water meter 100 can measure the capacitance of the subject as the physical characteristic (data regarding the water in the living body), thereby detecting the wetness of the armpit skin and calculating the amount of water in the body.

As illustrated in FIG. 1, the body water meter 100 includes a main body section 110 and an insert section 120. The main body section 110 forms a linear shape on the whole and includes an upper face 114, a lower face 115, and side faces 116 and 117, all of which are substantially parallel to the long axis (not illustrated) of the main body section 110. The main body section 110 has a housing that is provided with various user interfaces disposed on its surface and accommodates an electronic circuit that calculates the amount of water in the body.

Exemplary user interfaces illustrated in FIG. 1 include a power switch 111 and a display 112. The power switch 111 is disposed in a recess of a rear end surface 113 of the main body section 110. The configuration in which the power switch 111 is disposed in the recess can prevent erroneous operations of the power switch 111. When the power switch 111 is turned on, a power source 211 (see FIG. 2) that will be described below starts supplying electricity to individual units in the body water meter 100, causing the body water meter 100 to enter an operating state.

The display 112 is disposed on the side face 117 of the main body section 110 at a somewhat forward position along the long axis. When a measurer holds a gripping region 118 to measure the amount of water in a subject with the body water meter 100, the display 112 is not covered completely with the measurer's hand (the measurer can view the display 112 while holding the body water meter 100).

The display 112 shows a current measurement result 131 of the amount of water. In addition, the display 112 shows a preceding measurement result 132 for reference. A battery display part 133 shows the remaining power level of the battery (the power source 211 in FIG. 2). If the body water meter 100 acquires an invalid measurement result or detects a measurement error, the display 112 shows "E" and notifies a user of the detection of the measurement error. Letters and the like shown by the display 112 can be oriented correctly with the upper face 114 and lower face 115 of the main body section 110 facing upward and downward, respectively.

The insert section 120, in the body water meter 100, forms a slightly and downwardly curved shape, on the whole, with respect to the main body section 110, and includes an upper face 124 and a lower face 125 each having a curved surface. This insert section 120 has a tip surface 122 (that is an end surface opposite the rear end surface 113) provided with a sensor 121 retained slidably.

The sensor 121 has a contact surface 123 disposed substantially parallel to the tip surface 122. This sensor 121 is biased in the direction of an arrow 141b (e.g., at a force of about 150 gf) by a spring (not illustrated) so that it can be reliably pressed against the skin while in contact with it. When the entire contact surface 123 in the sensor 121 is pressed evenly against the armpit skin of the subject, and the sensor 121 is thereby slid by a predetermined distance (e.g., 1 mm to 10 mm, and 3 mm in this embodiment) in the direction of an arrow 141a (in a direction substantially orthogonal to the tip surface 122, or in a direction of the normal to the tip surface 122), the body water meter 100 is configured to start the measurement (the direction of the arrow 141a is referred to below as a slide direction).

More specifically, after the user turns on the power switch 111, to set the body water meter 100 in an operating state, when the sensor 121 is pressed in the direction of the arrow 141a by at least a predetermined distance, the body water meter 100 starts measuring the amount of water. In other words, after the user turns on the power switch 111 to set the body water meter 100 in an operating state, when the sensor 121 senses that the entire contact surface 123 is pressed evenly against the subject's armpit at a predetermined load (e.g., 20 gf to 200 gf, more preferably 100 gf to 190 gf, and 150 gf in this embodiment), the body water meter 100 starts measuring the amount of water. This mechanism enables the contact surface 123 in the sensor 121 to make contact with an armpit at a constant load during the measurement.

2. Functional Configuration of Body Water Meter 100

Figure 2:
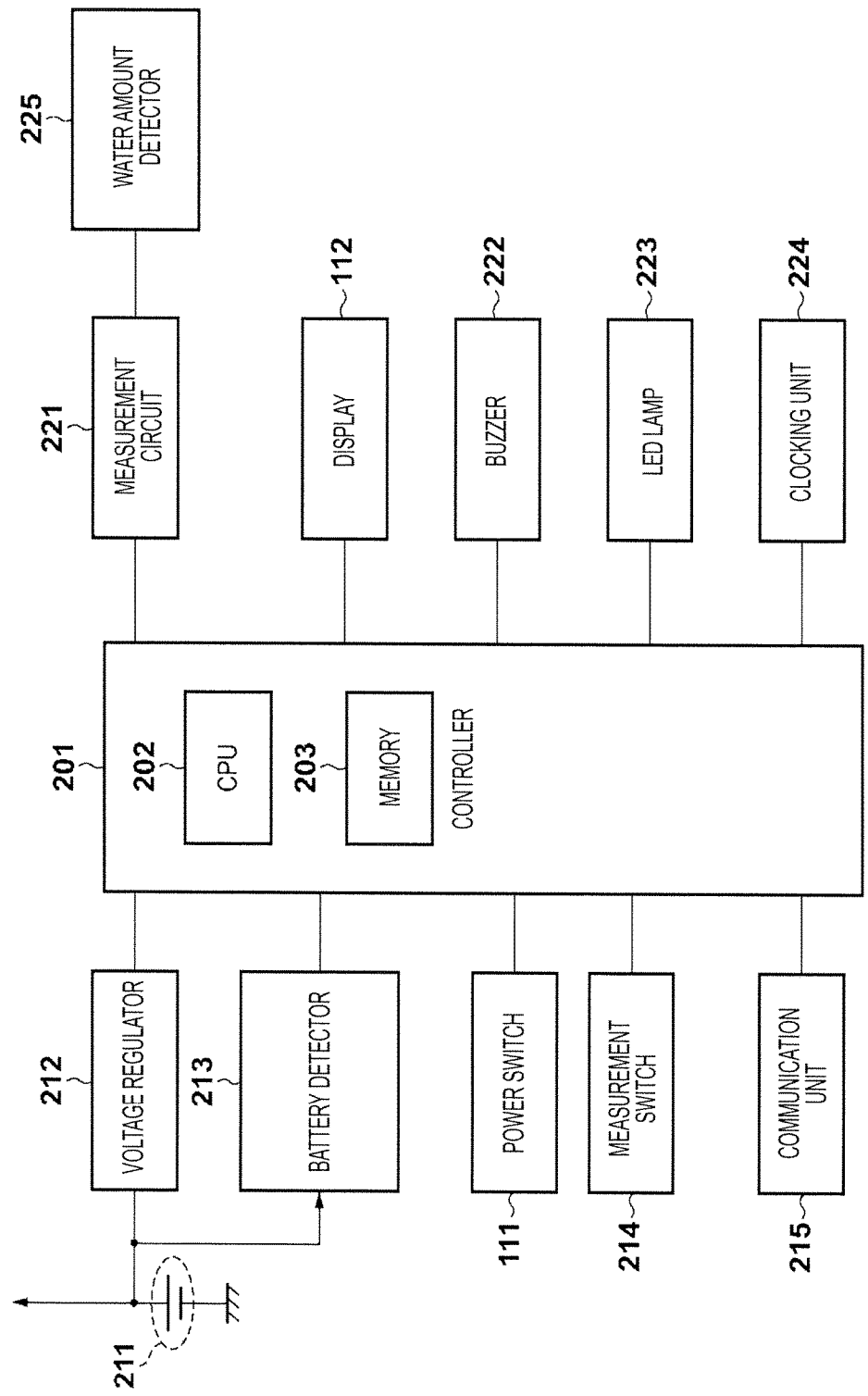
FIG. 2 is a view illustrating the functional configuration of the body water meter 100.

Next, the functional configuration of the body water meter 100 will be described. FIG. 2 is a block diagram of the functional configuration of the body water meter 100.

In FIG. 2, a controller 201 includes a Central Processing Unit (CPU) 202 and a memory 203; the CPU 202 executes programs stored in the memory 203, performing various controls in the body water meter 100.

For example, the CPU 202 controls the displaying operation of the display 112 and the driving of a buzzer 222 and an LED lamp 223, measures the amount of water (e.g., the capacitance in this embodiment), and determines the measurement result, all of which will be described later with reference to the flowcharts of FIGS. 5A and 5B. The memory 203 can include a nonvolatile memory and a volatile memory; the nonvolatile memory can be used as a program memory and the volatile memory can be used as a working memory of the CPU 202.

The power source 211 includes a replaceable or rechargeable battery and supplies electricity to the individual units in the body water meter 100. A voltage regulator 212 applies a constant voltage (e.g., 2.3 V) to the controller 201 and other units. A battery detector 213 detects a remaining battery level on the basis of the voltage of the power source 211 and notifies the controller 201 of the detection result. The controller 201 controls the display shown in the battery display part 133 on the basis of a battery level detection signal from the battery detector 213.

When the power switch 111 is depressed, the power source 211 starts supplying electricity to the individual units.

Then, when the controller 201 detects that a user keeps depressing the power switch 111 for at least one second, it maintains the electricity that the power source 211 supplies to the individual units, setting the body water meter 100 in an operating state. When the sensor 121 is pressed in the direction of the arrow 141a by at least a predetermined distance, a measurement switch 214 is turned on (in this case, the sensor 121 functions as a pressure detector that detects the depression). When the sensor 121 is pressed in the direction of the arrow 141a by at least a predetermined distance, the controller 201 starts measuring the amount of water. To reduce the consumption of the electricity from the power source 211, when the body water meter 100 has not started measuring the amount of water for two minutes since it was set in an operating state, the controller 201 automatically powers off the body water meter 100.

Figure 3:
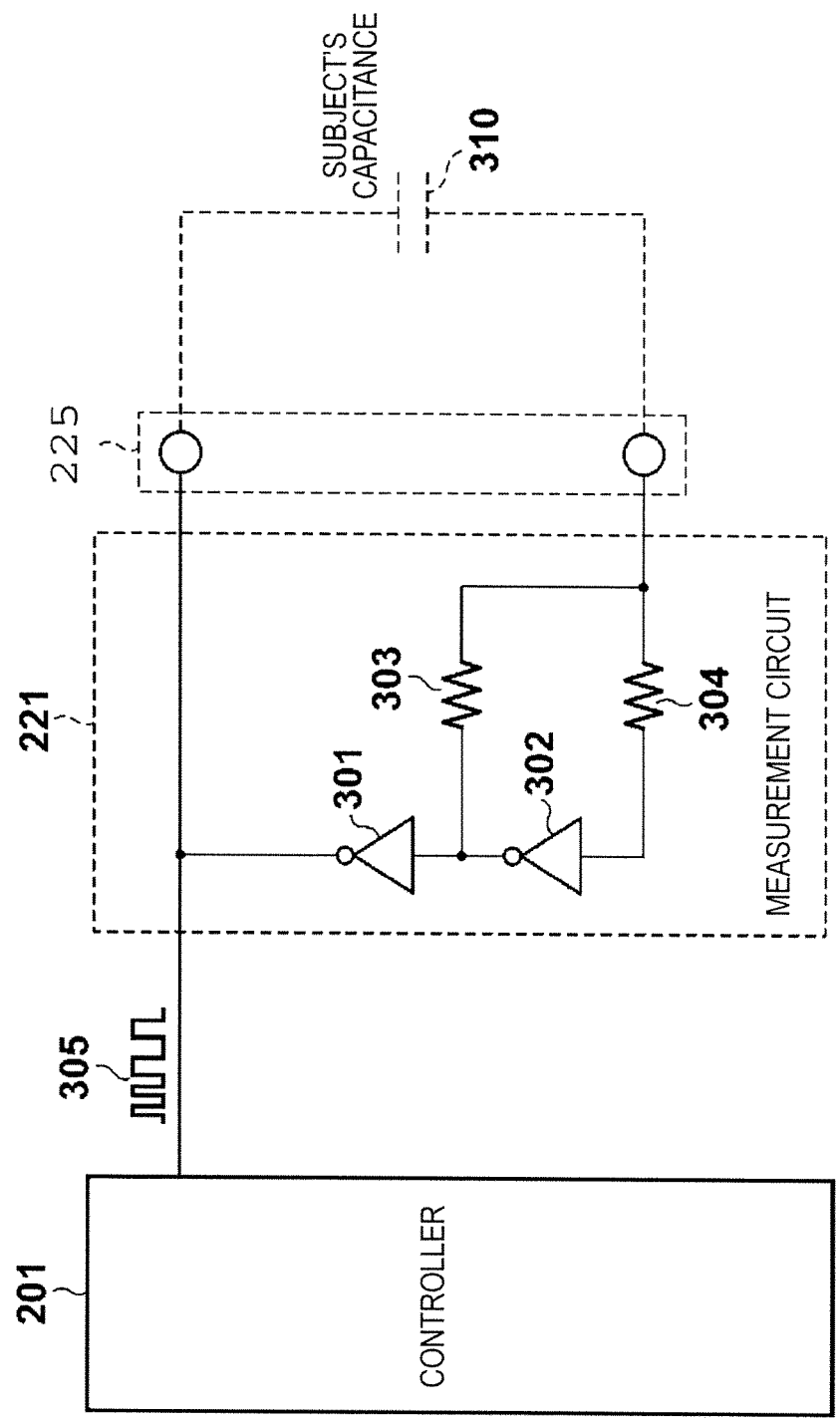
FIG. 3 is a diagram used to explain the measurement circuit in the body water meter 100.

A measurement circuit 221, which is connected to a water amount detector 225, measures capacitances. FIG. 3 is a diagram of an exemplary configuration of the measurement circuit 221. As illustrated in FIG. 3, inverters 301 and 302, resistors 303 and 304, and a subject's capacitance 310 configure a CR oscillation circuit. The controller 201 calculates the subject's capacitance 310 by measuring the oscillating frequency of an output signal 305 since the oscillating frequency of the output signal 305 changes depending on the subject's capacitance 310.

Referring back to FIG. 2, a communication unit 215 wirelessly transmits the measured water amount data to a server (not illustrated). In addition, the communication unit 215 acquires, from the server as appropriate, other pieces of living body information and the measurement results of other patients.

The display 112 provides a display having been described with reference to FIG. 1 under the control of the controller 201. The buzzer 222 sounds when the body water meter 100 starts and/or completes the measurement of the amount of water, informing a user that the measurement has started or been completed. The LED lamp 223 also fulfills the same informing function as the buzzer 222. More specifically, the LED lamp 223 illuminates when the body water meter 100 starts or completes the measurement of the amount of water, informing a user that the measurement has started or been completed. A clocking unit 224 operates by virtue of the electricity received from the power source 211 independently of on/off-state of the body water meter 100, and informs the controller 201 of what time it is when the body water meter 100 is in an operating state.

3. Overall Configuration of Management System

Next, a description will be given of an overall configuration of a management system that manages various pieces of living body information including the amount of water in a subject's body, which the body water meter 100 has measured.

Figure 4:
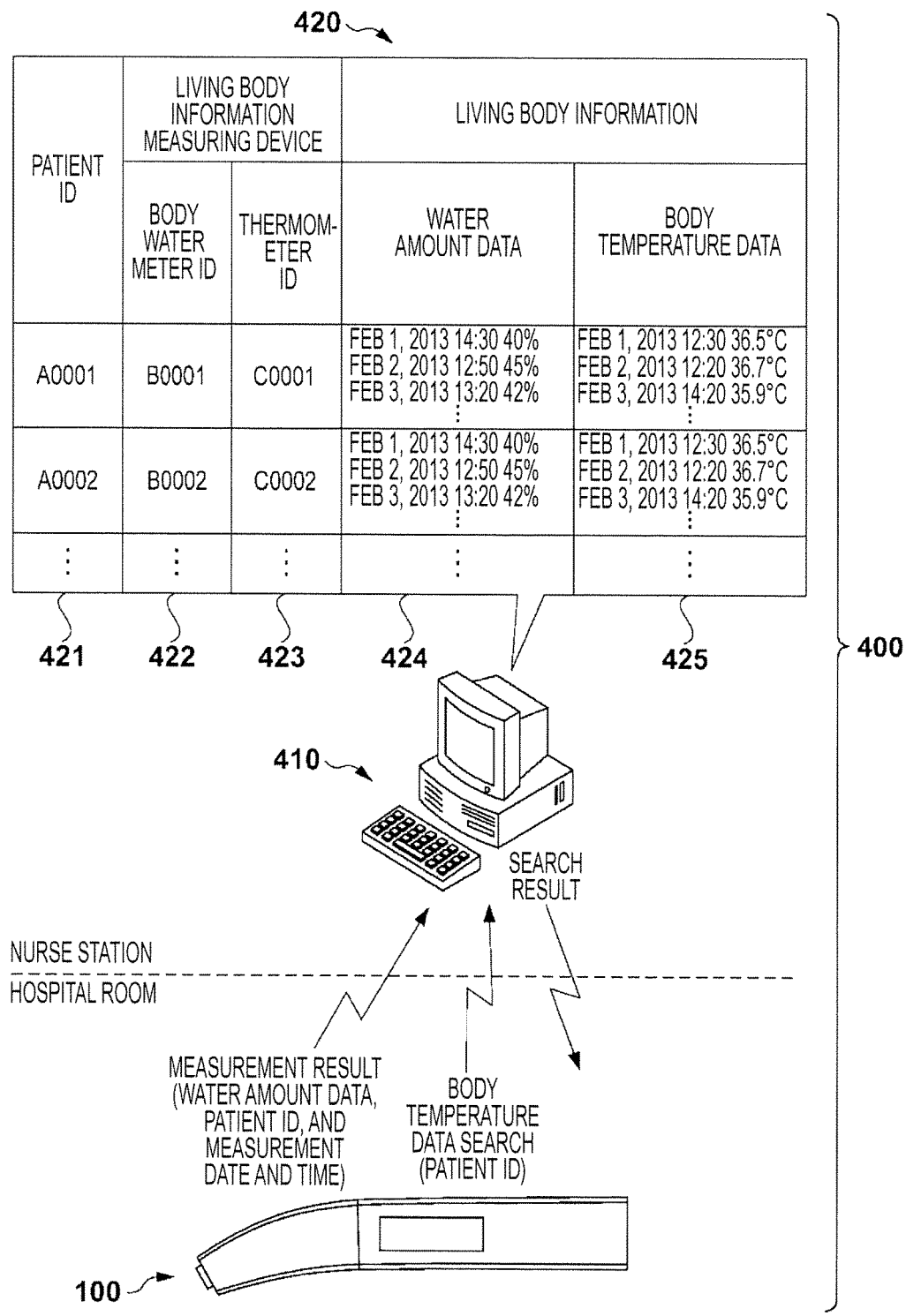
FIG. 4 is a view illustrating an overall configuration of a management system including the body water meter 100.

FIG. 4 is a view illustrating an overall configuration of a management system 400 including the body water meter 100. In FIG. 4, the reference numeral 410 denotes a server installed in, for example, a nurse station in a medical facility such as a hospital in which nurses and other medical staff members are working. This server 410 manages the living body information regarding inpatients.

The server 410 stores the living body information in a database 420 in relation to patients identifiers (IDs); the living body information is acquired from various living body information measuring devices including a body water meter and a thermometer, and the patients IDs serve as identifiers for use in identifying patients. The reference numeral 421 in the database 420 denotes patient IDs, and the reference numerals 422 and 423 therein are identifiers for use in identifying living body information measuring devices. More specifically, the reference numeral 422 denotes body water meter IDs and the reference numeral 423 thermometer IDs.

In the example in FIG. 4, different body water meters and thermometers are assumed to be used for different patients; however, the present invention is not limited to this configuration and a single living body information measuring device such as a body water meter or a thermometer may be shared among a plurality of patients.

The reference numerals 424 and 425 each denote living body information acquired by living body information measuring devices. More specifically, the reference numeral 424 denotes water amount data acquired by body water meters 100; the reference numeral 425 denotes body temperature data acquired by thermometers. Each of the water amount data 424 and the body temperature data 425 contains a measurement date and time and the measurement results in relation to each other.

The database 420 has been described regarding a case where body water meters and thermometers are used as living body information measuring devices; however, the present invention is not limited to this set of measurement devices or results and the database 420 may be configured to manage measurement results acquired by other types of living body information measuring devices.

The communication unit 215, described above, in the body water meter 100, can communicate with the server 410 to transmit or receive various types of data. For example, the body water meter 100 can be configured to receive the inputting of the patient ID of a subject prior to a measurement. When the body water meter 100 that has received the inputting of the patient ID measures the amount of water, the body water meter 100 adds the patient ID and measurement date and time to the measurement result and then transmits them to the server 410.

When the server 410 receives the measurement result from the body water meter 100, the server 410 relates this received measurement result to the measurement date and time and then stores them within a region of the database 420 corresponding to the patient ID contained therein.

The body water meter 100 is equipped with a function of, after having measured the amount of water in a subject's body, directing the server 410 to search for the latest body temperature data on this subject. For that purpose, the body water meter 100 transmits a body temperature data search command together with the patient ID.

When the server 410 receives the body temperature data search command from the body water meter 100, the server 410 searches the database 420 for the body temperature data that corresponds to the patient ID contained in the body temperature data search command and that contains a measurement date and time satisfying a predetermined measurement condition. Then, the server 410 transmits the search result to the body water meter 100. On the basis of the acquired water amount data and the body temperature data contained in the received search result, the body water meter 100 determines the condition of the subject comprehensively.

4. Process of Measuring and Determining Amount of Water Using Body Water Meter

A description will now be given of an operation (a process of measuring and determining the amount of water) performed by the body water meter 100, configured above, with reference to the flowcharts in FIGS. 5A and 5B.

Figure 5A:
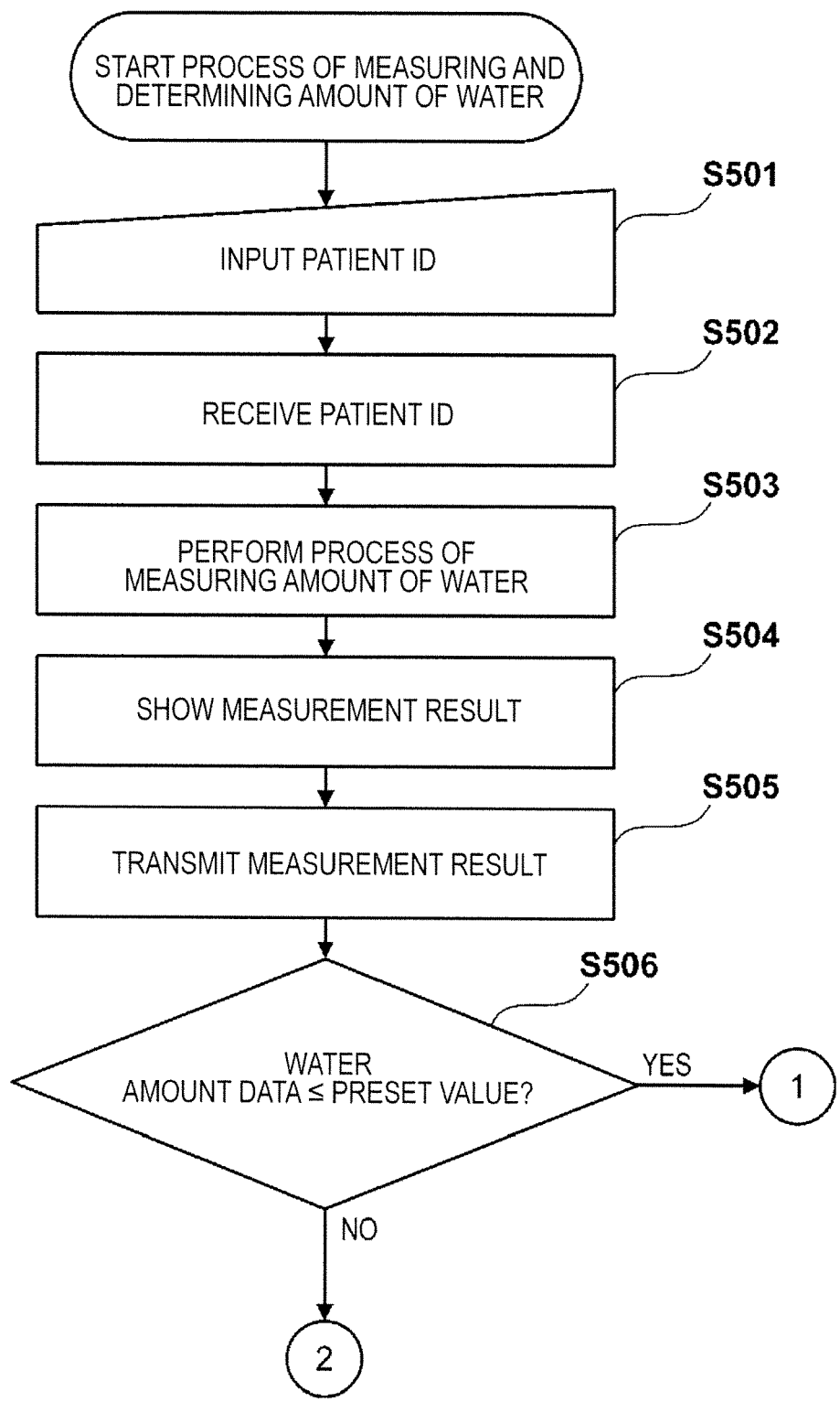
FIG. 5A is a flowchart of the processing through which the body water meter 100 measures and determines the amount of water in a patient's body.

When the power switch 111 is turned on, the body water meter 100 starts the process of measuring and determining the amount of water, as shown in FIGS. 5A and 5B.

At step S501, a measurer, such as a nurse, inputs the patient ID of a subject to the body water meter 100. At step S502, the body water meter 100 receives the patient ID that has been input at step S501.

At step S503, the measurer performs a process of measuring the amount of water in a subject's body by bringing an end 123 of the body water meter 100 into contact with the subject's armpit. After the measurer has completed the process of measuring the amount of water, the display 112 shows the measurement result, at step S504. Then, the processing proceeds to step S505, and the communication unit 215 wirelessly transmits the measurement result to the server 410 together with the patient ID, recognized at step S502, and the measurement date and time.

At step S506, the controller 201 determines whether the water amount data acquired through the measurement of the amount of water at step S503 is equal to or less than a preset value (e.g., 35%). If the water amount data is determined to be equal to or less than the preset value at step S506, the processing proceeds to step S511, in FIG. 5B. If the water amount data is determined to exceed the preset value at step S506, the body water meter 100 concludes the process of measuring and determining the amount of water.

At step S511 in FIG. 5B, the communication unit 215 transmits a body temperature data search command to the server 410 together with the patient ID. When the server 410 receives the body temperature data search command, the server 410 searches the database 420 for body temperature data that is stored in relation to the patient ID contained in the search command and that has been acquired within a predetermined period of time (24 hours) before the current time. If the server 410 extracts the body temperature data through the search process, the server 410 transmits the extracted body temperature data to the body water meter 100 as a search result.

At step S512, the controller 201 determines whether the body temperature data that has been acquired within the past predetermined period of time is equal to or more than a preset value (threshold), such as 37° C., on the basis of the search result received from the server 410. If the body temperature data is determined to be less than 37° C. at step S512, the processing proceeds to step S515, and then the display 112 shows the received body temperature data in addition to already showing the water amount data. After that, the body water meter 100 concludes the process of measuring and determining the amount of water.

If the body temperature data is determined to be equal to or more than 37° C. at step S512, the processing proceeds to step S513. In the case where the water amount data on the subject is 35% or below and the body temperature data is 37° C. or above, the body water meter 100 determines that this subject is in a potentially serious condition, at step S513. At step S514, the body water meter 100 outputs a message (warning) that the subject is in a potentially serious condition. The above threshold may be varied as appropriate in steps of 0.1° C. depending on a subject type (e.g., an elderly person, infant, etc.). Furthermore, the threshold may be set in accordance with the normal body temperature of each subject which has been measured in advance.

At step S515, the display 112 shows the body temperature data in addition to already showing the water amount data. After that, the body water meter 100 concludes the process of measuring and determining the amount of water. If the subject is suspected of having an infection, the display 112 may output a message that he/she is suspected of having an infection, in addition to the water amount data and the body temperature data. Alternatively, the body water meter 100 may tie information that a subject is suspected of having an infection to the water amount data or the body temperature data, and then store them.

As is evident from the above description, a body water meter 100 can be configured to, if a measurement result is equal to or less than a preset value, access a server and refer to the latest body temperature data on this subject. Moreover, if the measurement result is equal to or less than the preset value and the latest body temperature data on the subject is equal to or more than a preset value, the body water meter 100 is configured to output a message that the subject is in a potentially serious condition.

As described above, a body water meter 100 reflects body temperature data in living body information other than water amount data, making it possible to determine the condition of a subject comprehensively.

The embodiments described above employ the configuration in which only if the measurement result of a subject is at a preset value or less, a body water meter accesses a server and refers to the body temperature data on the subject; however, the present invention is not limited to this configuration. For example, first a body water meter may refer to the body temperature data on a subject and then measure the amount of water in the subject's body. Subsequently, after having completed the measurement of the amount of water, the body water meter may determine the condition of the subject comprehensively and swiftly. Details of additional or alternative embodiments will be described below. It should be noted that the following description will focus on differences from the above embodiments.

Figure 6A:
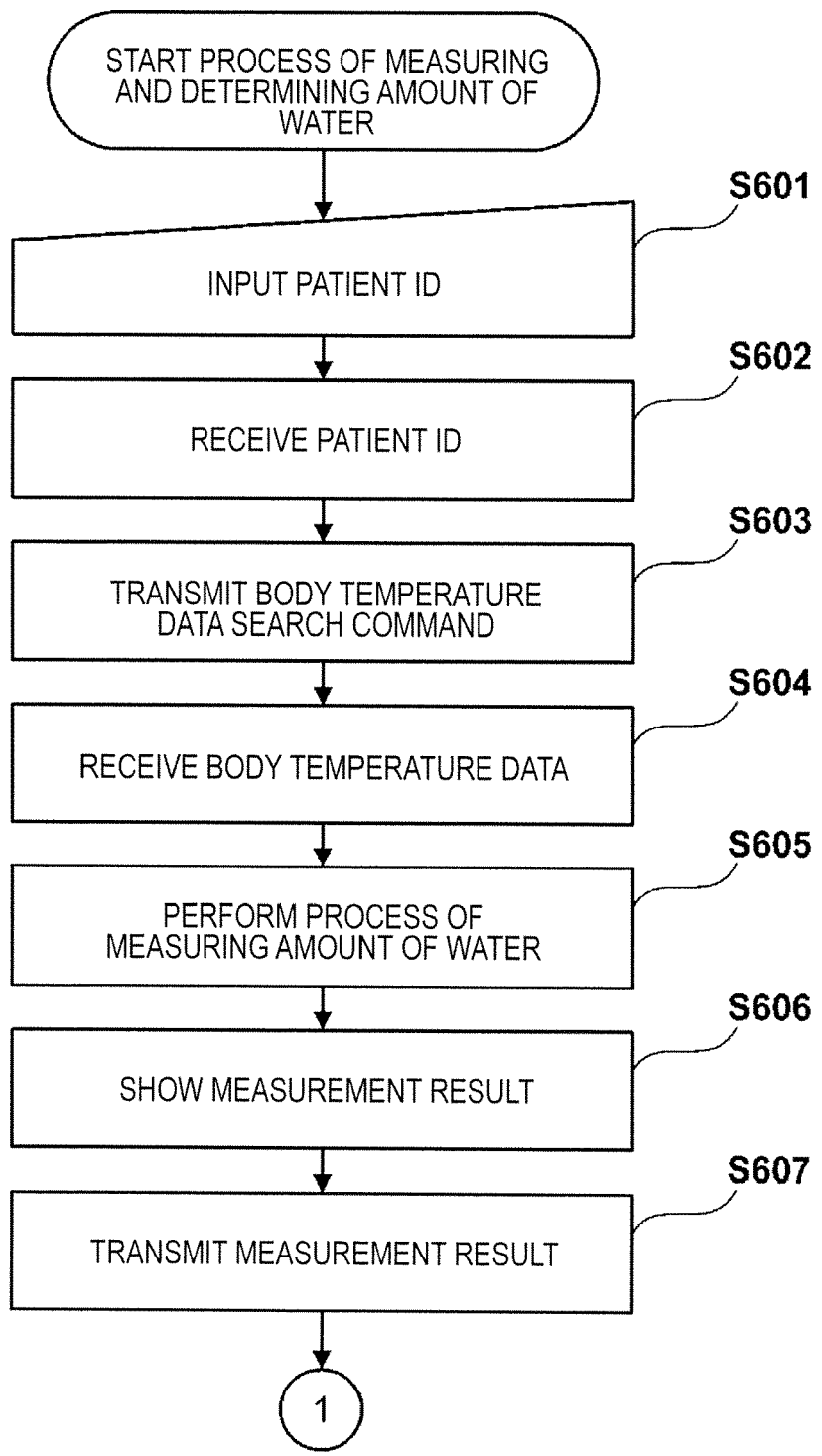
FIG. 6A is a flowchart of the processing through which a body water meter 100 measures and determines the amount of water in a patient's body.

FIGS. 6A and 6B are flowcharts of the processing through which a body water meter 100 measures and determines the amount of water.

When a power switch 111 is turned on, the body water meter 100 according to this embodiment starts the process of measuring and determining the amount of water, as shown in FIGS. 6A and 6B.

At step S601, a measurer, such as a nurse, inputs the patient ID of a subject to the body water meter 100. At step S602, the body water meter 100 receives the patient ID that has been input at step S601.

At step S603, a communication unit 215 transmits a body temperature data search command to a server 410 together with the patient ID. When the server 410 receives the body temperature data search command, it searches a database 420 for the body temperature data that is stored in relation to the patient ID contained the search command and that has been acquired within a predetermined period of time (24 hours) before the current time.

If the server 410 extracts the body temperature data through the search process, the server 410 transmits the extracted body temperature data to the body water meter 100 as a search result. At step S604, the communication unit 215 receives the body temperature data transmitted from the server 410, as the search result.

At step S605, a measurer performs a process of measuring the amount of water in the subject's body by bringing an end 123 of the body water meter 100 into contact with the subject's armpit. After the measurer has completed the process of measuring the amount of water, the display 112 shows the measurement result at step S606. The processing subsequently proceeds to step S607, and the communication unit 215 wirelessly transmits the measurement result to the server 410 together with the patient ID, recognized at step S602, and the measurement date and time.

At step S611, the controller 201 determines whether the body temperature data that has been acquired from the server 410 as the search result at step S604 is equal to or more than 37° C. If the body temperature data is determined to be less than 37° C. at step S611, the processing proceeds to step S615, and then the display 112 shows the received body temperature data in addition to already showing the water amount data. After that, the body water meter 100 concludes the process of measuring and determining the amount of water.

If the body temperature data is determined to be equal to or more than 37° C. at step S611, the processing proceeds to step S612. At step S612, the controller 201 determines whether the water amount data acquired through the measurement of the amount of water at step S605 is equal to or less than a preset value (e.g., 35%).

If the water amount data is determined to exceed the preset value at step S612, the processing proceeds to step S615. Then, the display 112 shows the received body temperature data in addition to already showing the water amount data. After that, the body water meter 100 concludes the process of measuring and determining the amount of water.

If the water amount data is determined to be equal to or more than the preset value at step S612, the processing proceeds to step S613. In the case where the water amount data on the subject is 35% or below and the body temperature data is 37° C. or above, the body water meter 100 determines that this subject is in a potentially serious condition, at step S613.

At step S614, the body water meter 100 outputs a message that the subject is in a potentially serious condition. At step S615, the display 112 shows the received body temperature data in addition to already showing the water amount data.

As is evident from the above description, a body water meter 100 can be configured to, before measuring the amount of water in a subject's body, access a server and refer to the latest body temperature data on this subject. Moreover, if the measurement result of the amount of water is equal to or less than a preset value and the latest body temperature data on the subject is equal to or more than a preset value, the body water meter 100 may be configured to output a message promptly that the subject is in a potentially serious condition.

As described above, a body water meter 100 reflects body temperature data in living body information other than water amount data, making it possible to determine the condition of a subject comprehensively.

The embodiments described above are configured to require the inputting of a patient ID; however, the present invention is not limited to this configuration. For example, in the case where different body water meters are used for different patients and the server 410 stores patient IDs in relation to corresponding body water meter IDs, a measurer can measure the amounts of water without inputting patient IDs. In this case, each body water meter is configured to transmit a measurement result containing water amount data, measurement date and time, and body water meter ID.

The embodiments described above are configured to determine the condition of a subject comprehensively from both water amount data and body temperature data. The present invention is, however, not limited to this configuration. For example, embodiments may be configured to determine whether the water amount data on a subject differs from typical water amount data and, if it differs, further determine whether this difference is ascribable to the subject or his/her surroundings. Details of this embodiment will be described below.

Figure 7A:
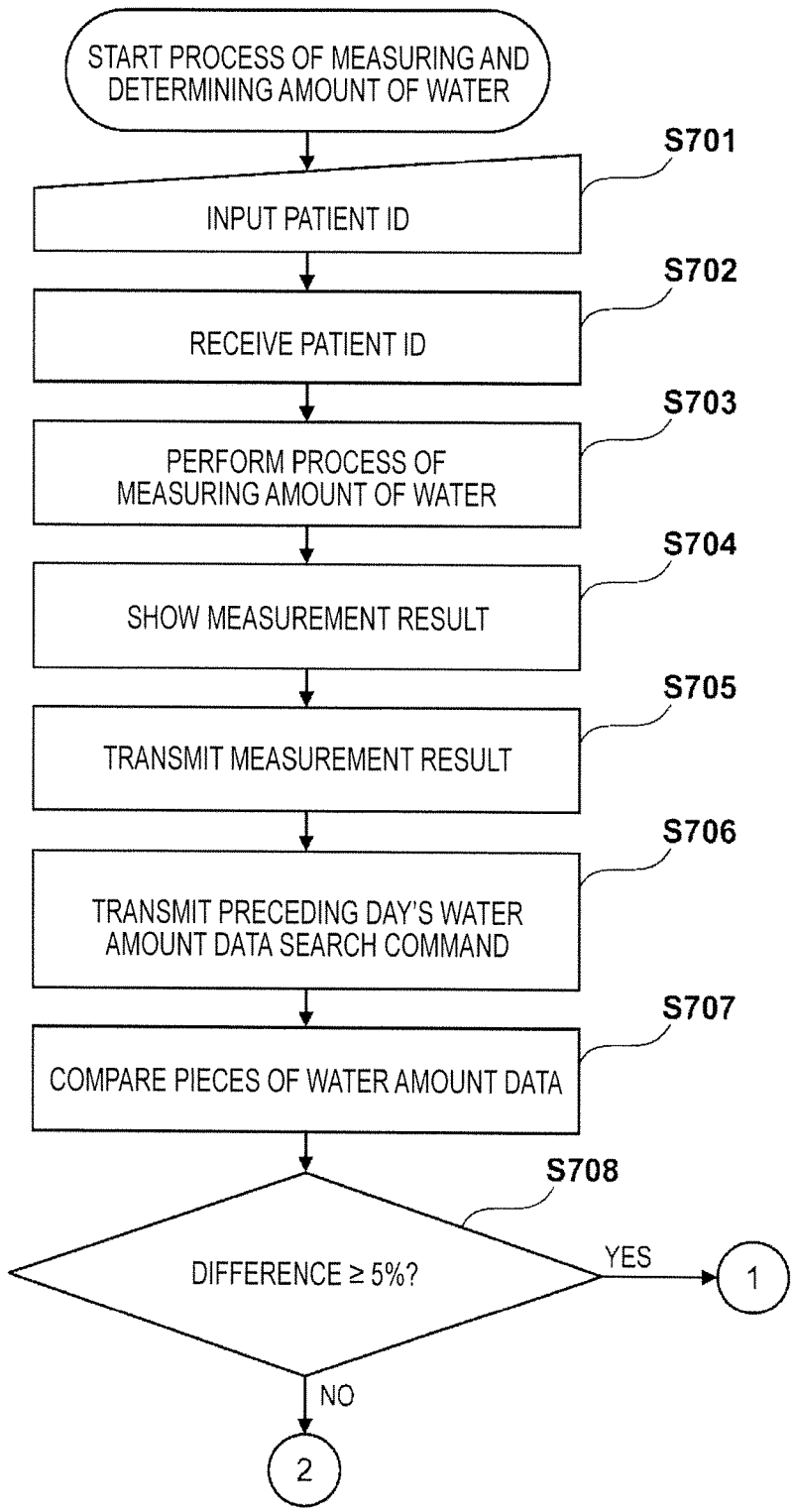
FIG. 7A is a flowchart of the processing through which a body water meter 100 measures and determines the amount of water in a patient's body.

FIGS. 7A and 7B are flowcharts of the processing through which a body water meter 100 measures and determines the amount of water.

When a power switch 111 is turned on, the body water meter 100 starts the process of measuring and determining the amount of water, as shown in FIGS. 7A and 7B.

At step S701, a measurer, such as a nurse, inputs the patient ID of a subject to the body water meter 100. At step S702, the body water meter 100 receives the patient ID that has been input at step S701.

At step S703, the measurer performs a process of measuring the amount of water in a subject's body by bringing an end of the body water meter 100 into contact with the subject's armpit. After the measurer has completed the process of measuring the amount of water, a display 112 shows the measurement result at step S704. Then, the processing proceeds to step S705, and the communication unit 215 wirelessly transmits the measurement result to a server 410 together with the patient ID, recognized at step S702, and the measurement date and time.

At step S706, a controller 201 directs the server 410 to search for water amount data that contains a patient ID identical to the patient ID having been transmitted at step S705 and that was acquired on the preceding day (measured on the preceding day) (transmits preceding day's water amount data search command).

When the server 410 receives the preceding day's water amount data search command from the body water meter 100, the server 410 searches a database 420 and then transmits the search result to the body water meter 100. More specifically, the server 410 searches the database 420 for water amount data that contains a patient ID identical to the patient ID contained in the preceding day's water amount data search command and that was acquired on the preceding day. Then, the server 410 wirelessly transmits this search result to the body water meter 100.

At step S707, the controller 201 compares the search result (the water amount data containing the identical patient ID and acquired on the preceding day) received from the server 410 with the current measurement result (the water amount data acquired at step S703).

At step S708, the controller 201 determines whether, as the result of the comparison at step S707, the ratio of the preceding day's water amount data to the current water amount data is equal to or more than a preset proportion (e.g., 50).

If the determination result at step S708 indicates that the ratio is less than the preset proportion, the body water meter 100 concludes the process of measuring and determining the amount of water. If the determination result at step S708 indicates that the ratio is equal to or more than the preset proportion, the processing proceeds to step S711 (FIG. 7B).

At step S711, the controller 201 directs the server 410 to search for the water amount data on other patients belonging to the same group as the current subject (transmits other patients' water amount data search command).

The expression "other patients belonging to the same group as the current subject" refers to other patients present in the same surroundings as the current subject, such as in the same hospital room or on the same floor. Patients belonging to the same group are assigned the same group ID [not shown] in the database 420. The respective pieces of water amount data on the other patients contain today's measurement results and preceding day's measurement results of the other patients.

In response to the other patients' water amount data search command transmitted at step S711, the server 410 searches for today's measurement results and the preceding day's measurement results of the water amount data on the other patients who belong to the group with the patient ID transmitted at step S705. Then, the server 410 transmits the search result (the respective pieces of water amount data on the other patients in the same group) to the body water meter 100.

At step S712, the controller 201 calculates the difference between the preceding day's water amount data and today's water amount data of each of the other patients, on the basis of the search result received from the server 410.

At step S713, the controller 201 counts the number of patients for which the differences calculated at step S712 are equal to or more than a preset proportion (e.g., 5%). At step S714, the controller 201 determines whether the number of patients counted at step S713 accounts for a preset amount (e.g. at least 50%) of the total number of patients in the same group.

If the number of patients counted is determined not to account for at least 50% of the total at step S714, the processing proceeds to step S716. In this case, the controller 201 determines that the marked difference between the current measurement result and preceding day's measurement result of the subject is ascribable to the subject.

If the number of patients counted is determined to account for at least 50% at step S714, the processing proceeds to step S715. In this case, the controller 201 determines that the marked difference between the current measurement result and preceding day's measurement result of the subject is ascribable to the surroundings of the subject. Then, the body water meter 100 outputs a message that encourages an improvement in the surroundings.

For example, if the measurement result of patients in the same hospital room varies in such a way that the amount of water in their bodies decreases uniformly, the controller 201 determines that their surroundings are problematic, such as excessively hot or dry, and no problem lies in the subject accordingly. In this case, a measurer can protect the patient from undergoing dehydration or some other disease by improving the surroundings.

After having completed the process at step S715 or S716, the body water meter 100 concludes the process of measuring and determining the amount of water.

As is evident from the above description, a body water meter 100 can be configured to, after having completed the measurement of the amount of water in a subject's body, access a server and calculate the difference from a preceding day's measurement result. Moreover, the body water meter 100 can be configured to, if the difference from the preceding day's measurement result is equal to or higher than a preset proportion, access the server again and calculate the differences between the preceding day's measurement results and today's measurement results of other patients who belong to the same group as the subject.

The body water meter 100 can be configured to determine whether the difference in the measurement result of the subject is ascribable to the subject or the subject's surroundings. If the body water meter 100 determines that the surroundings are problematic, the body water meter 100 is configured to output a message about the problem to a measurer.

Consequently, the body water meter 100 enables a measurer to determine comprehensively the measurement results of subjects and treat the subjects appropriately.

The embodiments described above are configured such that a body water meter 100 communicates directly with a server 410; however, the present invention is not limited to this configuration. For example, one embodiment may be configured such that fixed terminals assigned to respective patients in hospital rooms and connected to a server communicate with a body water meter.

Figure 8:
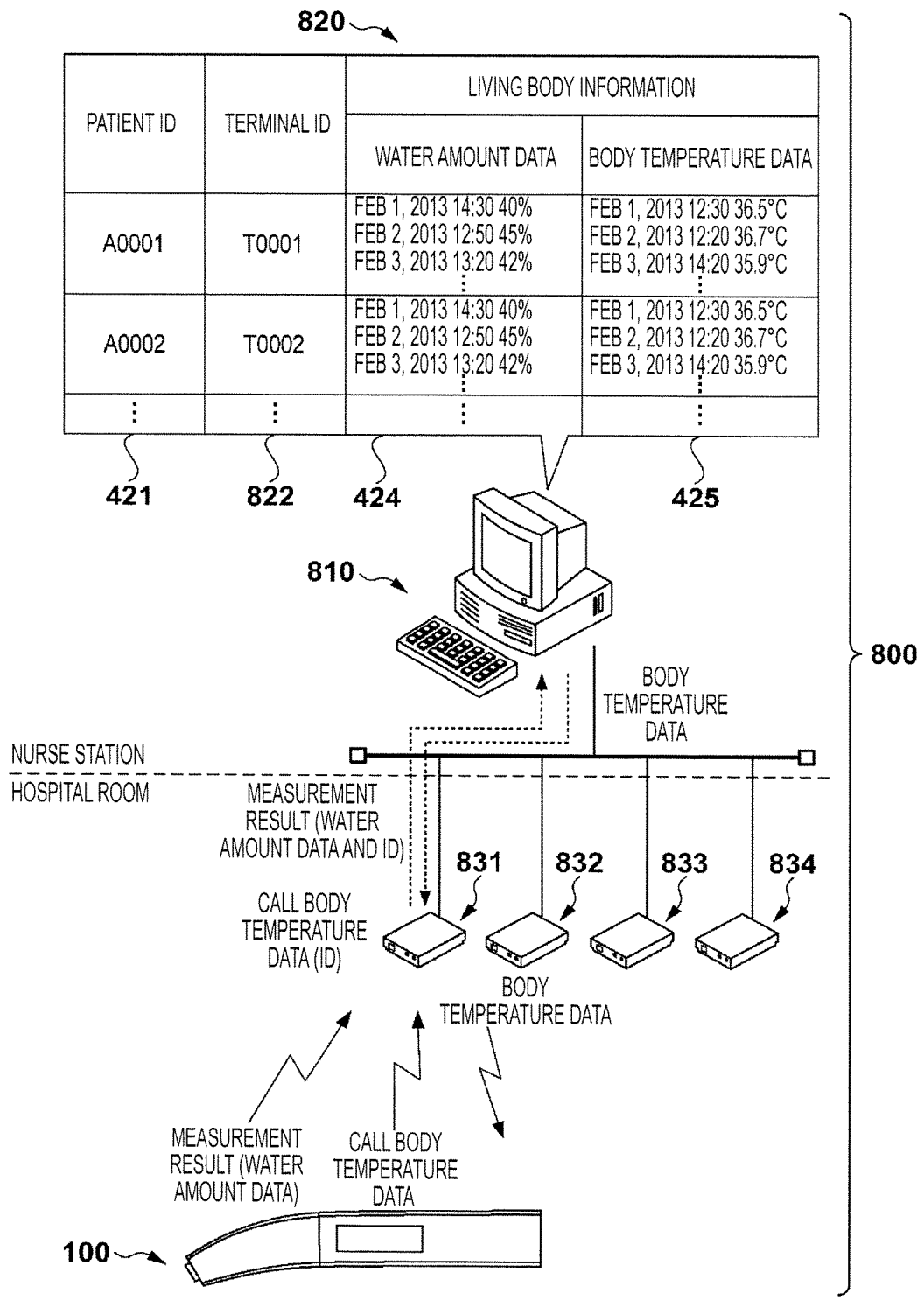
FIG. 8 is a view illustrating an overall configuration of a management system including a body water meter 100.

FIG. 8 illustrates an overall configuration of a management system 800 including a body water meter 100. In FIG. 8, the reference numeral 810 denotes a server installed in, for example, a nurse station in a medical facility such as a hospital in which nurses and other medical staff members are working. This server 810 manages the living body information regarding inpatients.

The server 810 fulfills the same function as the server 410 having been described in conjunction with FIG. 4. The management system 800 includes dedicated fixed terminals arranged one-to-one for patients in hospital rooms. A database 820 contains terminal IDs (822) for use in identifying the fixed terminals and patient IDs (421) for use in identifying the patients corresponding to the fixed terminals; the terminal IDs (822) and the patient IDs (421) are related to each other.

The server 810 identifies from which fixed terminal water amount data or body temperature data is transmitted, thereby finding with which patient this water amount data or body temperature data is associated. Then, the server 810 stores the water amount data or body temperature data in a predetermined region in the database 820.

The reference numerals 831 to 834 denote fixed terminals that correspond one-to-one to patients in hospital rooms, and installed and fixed, for example, near beds. These fixed terminals 831 to 834 each have a unique terminal ID and are managed in the database 820 as described above.

The fixed terminals 831 to 834 have the same function. For example, when the body water meter 100 that has completed the measurement of the amount of water is positioned close to the fixed terminal 831, the fixed terminal 831 communicates with the body water meter 100, receiving a measurement result therefrom. The fixed terminal 831 then transmits the received measurement result to the server 810 together with a terminal ID.

When the body water meter 100 is positioned close to the fixed terminal 831 while outputting a predetermined command, such as a body temperature data search command, the fixed terminal 831 receives this command therefrom. The fixed terminal 831 then transmits the received command to the server 810 together with the terminal ID. When the fixed terminal 831 receives a search result from the server 810, the server 810 transmits this search result to the body water meter 100.

As is evident from the above description, a management system includes: dedicated fixed terminals that correspond one-to-one to patients in hospital rooms; and a body water meter that communicates with the fixed terminal. This configuration allows for the same processing as the foregoing embodiments and can produce the same effects.

The embodiment described above is configured such that dedicated fixed terminals are installed one-to-one for patients in hospital rooms; however, the present invention is not limited to this configuration. One embodiment may be configured such that a nurse or medial staff member may carry a dedicated terminal with him/her.

Figure 9:
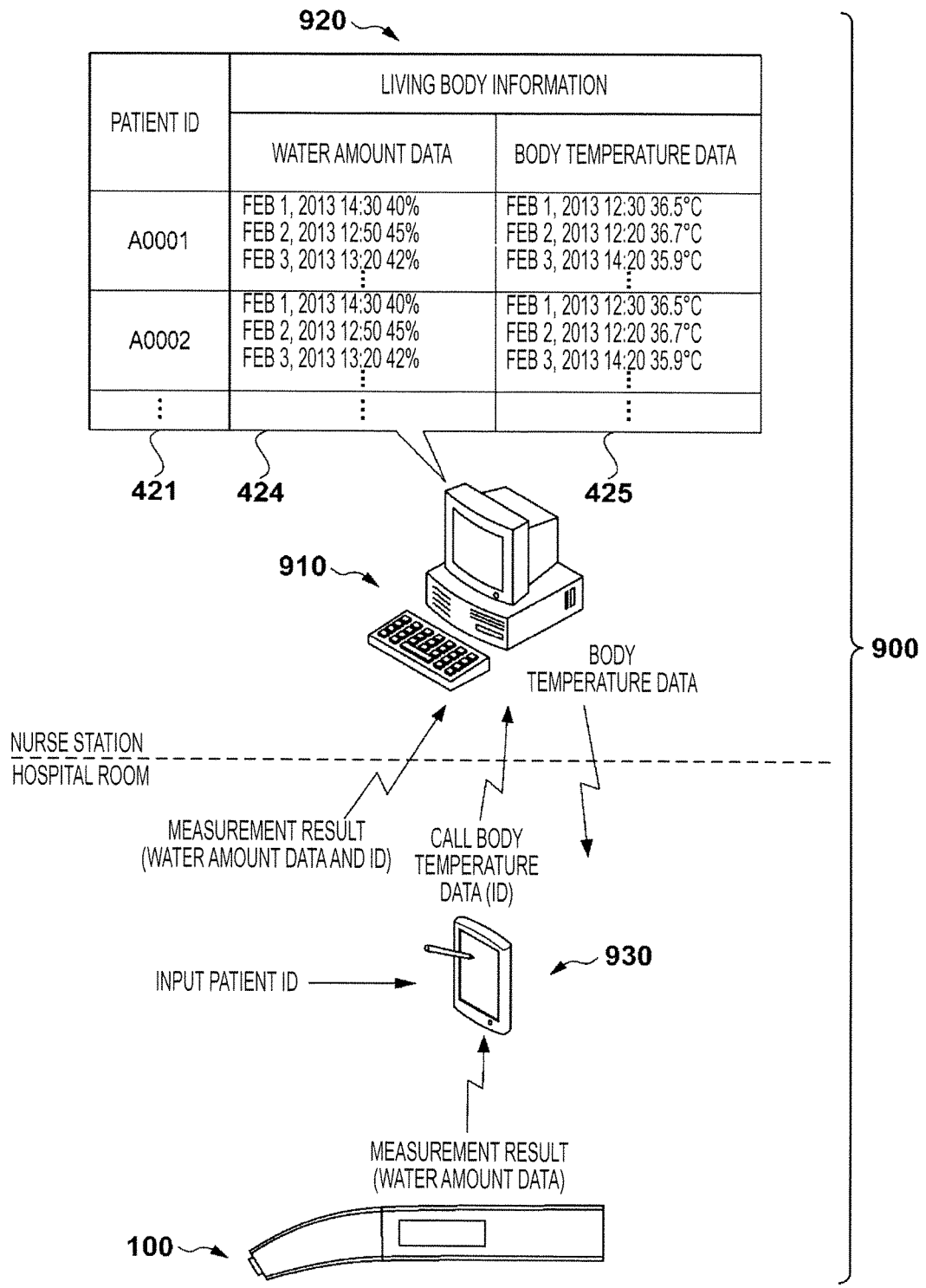
FIG. 9 is a view illustrating an overall configuration of a management system including a body water meter 100.

FIG. 9 illustrates an overall configuration of a management system 900 including a body water meter 100. In FIG. 9, the reference numeral 910 denotes a server installed in, for example, a nurse station in a medical facility such as a hospital in which nurses and other medical staff members are working. This server 910 manages the living body information regarding inpatients.

The server 910 fulfills the same function as the server 410 having been described in conjunction with FIG. 4. The management system 900 is, however, configured such that each nurse or staff member carries a mobile terminal 930. First, a nurse or staff member inputs the patient ID of a subject to the mobile terminal 930, and then the body water meter 100 inputs the measurement result of living body information thereto. This process allows the mobile terminal 930 to transmit various pieces of living body information containing patients ID to the server 910. A database 920 stores a patient ID (421) and pieces of living body information (424 and 425) in relation to one another.

The reference numeral 930 denotes a mobile terminal, which is carried by each nurse or staff member who moves around hospital rooms. For example, the nurse inputs the patient ID of a subject to the mobile terminal 930 and then measures the amount of water in the subject's body with the body water meter 100. Then, when the mobile terminal 930 receives, from the body water meter 100, the measurement result of the amount of water measured by the body water meter 100, the mobile terminal 930 adds the input patient ID to the measurement result and transmits the data to the server 910.

When the mobile terminal 930 receives various commands, including a body temperature data search command, from the body water meter 100, the mobile terminal 930 adds a patient ID to these commands and transmits them to the server 910. In addition, when the mobile terminal 930 receives search results from the server 910, the mobile terminal 930 transmits them to the body water meter 100.

As is evident from the above description, a management system, which is configured such that a nurse or some other medical staff member carries a mobile terminal that receives a measurement result from a body water meter, allows for the same processing as the foregoing embodiments and can produce the same effects.

The embodiment above is configured such that a mobile terminal 930 functions as a relay that connects a body water meter 100 to a server 910; however, the present invention is not limited to this configuration. For example, the mobile terminal 930 may be configured to perform the process at step S506 and subsequent processes in FIG. 5A, the process at step S611 and subsequent processes in FIG. 6B, or the process at step S706 and subsequent processes in FIG. 7A.

Some of the embodiments above have been described regarding the case where body temperature data is acquired as another piece of living body information. However, another piece of living body information for use in determining comprehensively the measurement result of the amount of water in a living body is not limited to body temperature data. For example, arterial oxygen saturation ($SpO_2$) may be acquired in addition to or instead of body temperature data.

The present invention is not limited the foregoing embodiments and can be modified and varied in various ways without departing from the spirit and scope of the invention. Therefore, the following claims are appended to disclose the scope of the invention.

The invention claimed is:

1. A body water meter that measures an amount of water in a body of a subject, the body water meter comprising:
   direction means for, when water amount data is acquired through the measurement of the amount of water in the body of the subject, providing an identification of the subject to a server that manages data regarding pieces of living body information for the subject and directing the server to search, based on the identification provided, for other data acquired through measurement of living body information for the subject other than the amount of water, the other data satisfying a predetermined measurement condition;
   receiving means for receiving the other data from the server;
   processing means for determining a condition of the subject based on the water amount data for the subject and the other data received from the server; and
   output means for outputting a message indicating the condition of the subject based on both the water amount data and the other data.

2. The body water meter according to claim 1, wherein the other data is body temperature data acquired through measurement of a body temperature of the subject.

3. The body water meter according to claim 2, wherein, when the water amount data is equal to or less than a first preset value, the direction means directs the search for the body temperature data.

4. The body water meter according to claim 3, wherein the direction means directs the search for the body temperature data that had been measured within a predetermined period of time before a measurement date and time at which the water amount data was measured.

5. The body water meter according to claim 4, wherein when the water amount data is equal to or less than the first preset value and the body temperature data is equal to or more than a second preset value, the output means outputs a message that the subject is in a potentially serious condition.

6. The body water meter according to claim 5, further comprising:
   transmission means for transmitting the water amount data acquired through the measurement of the amount of water in the body of the subject to the server, and
   wherein the direction means further directs the server to store the water amount data in a predetermined region of a database of the server associated with and based on the identification of the subject.

7. A terminal that communicates with a body water meter that measures an amount of water in a subject's body, the terminal comprising:
   direction means for, when receiving, from the body water meter, water amount data acquired through a measurement of the amount of water in the subject's body, directing a server that manages pieces of living body information for the subject to search for other data acquired through measurement of living body information on the subject other than the amount of water, the other data satisfying a predetermined measurement condition; and
   output means for outputting a message indicating a condition of the subject which is determined on the basis of both the water amount data and the other data on the subject.

8. A body water meter that measures an amount of water in a subject's body, the body water meter comprising:
   a measurement circuit to measure a first amount of water in the subject's body;

a communication unit in communication with a server, the communication unit operable to:
transmit water amount data to the server;
transmit search direction to the server; and
receive water amount data from the server;
a processor in communication with the measurement circuit and the communication unit, the processor operable to:
receive the measurement of the first amount of water in the subject's body from the measurement circuit;
determine first water amount data based on the measurement;
provide the first water amount data to the communication unit to transmit to the server;
provide a first direction to the communication unit to transmit the server, wherein the first direction directs the server to search for second water amount data, the second water amount data being water amount data that had been measured before a measurement date on which the first amount of water in the subject's body was measured;
determine whether a difference between the first water amount data and the second water amount data is equal to or more than a preset value;
when the difference between the first water amount data and the second water amount data is equal to or more than a preset value, provide a second direction to the communication unit to transmit the server, wherein the second direction directs the server to search for third water amount data and fourth water amount data, wherein the third water amount data is water amount data associated with at least one other subject belonging to a same group as the subject, and wherein the third water amount data is measured on a same day as the measurement the first amount of water in the subject's body, wherein the fourth water amount data is water amount data that had been measured before a measurement date on which the third water amount data was measured;
determine whether a second difference between the third water amount data and the fourth water amount data received in response to the second direction is similar to the difference between first water amount data and the second water amount data; and
a display in communication with the processor, the display operable to:
when the second difference between the third water amount data and the fourth water amount data received in response to the second direction is similar to the difference between the first water amount data and the second water amount data, output a message that the difference between the first water amount data and the second water amount data is ascribable to surroundings of the subject.

9. A terminal that communicates with a body water meter that measures an amount of water in a subject's body, the terminal comprising:
transmission means for, when receiving first water amount data acquired through the measurement of the amount of water in the subject's body, transmitting the first water amount data to a server;
first direction means for directing the server to search for second water amount data, the second water amount data being water amount data that had been measured before a measurement date on which the first water amount data was measured;
second direction means for, when a different between the first water amount data and the second water amount data received in response to the direction from the first direction means is equal to or more than a preset value, directing the server to search for third water amount data and fourth water amount data, the third water amount data being water amount data on other subjects belonging to a same group as the subject and being measured on a same day as the measurement date of the first water amount data, the fourth water amount data being water amount data that had been measured before a measurement date on which the third water amount data was measured; and
output means for, when one or more of the other subjects for which a difference between the third water amount data and the fourth water amount data received in response to the direction from the second direction means account for a preset proportion or more, outputting a message that a difference between the first water amount data and the second water amount data on the subject is ascribable to surroundings of the subject.

10. The body water meter according to claim 8, wherein the processor is further operable to:
provide a third direction to the communication unit to direct the server to search for other data acquired through measurement of living body information on the subject other than the amount of water, the other data satisfying a predetermined measurement condition;
receive the other data; and
determine a condition of the subject based on both the water amount data and the other data.

11. The body water meter according to claim 10, wherein the display is further operable to output a message indicating the condition of the subject.

12. The body water meter according to claim 11, wherein the other data is body temperature data acquired through measurement of a body temperature of the subject.

13. The body water meter according to claim 12, wherein, when the water amount data is equal to or less than a first preset value, the direction means directs the search for the body temperature data.

14. The body water meter according to claim 13, wherein the direction means directs the search for the body temperature data that had been measured within a predetermined period of time before a measurement date and time at which the water amount data was measured.

15. The body water meter according to claim 14, wherein, when the water amount data is equal to or less than the first preset value and the body temperature data is equal to or more than a second preset value, the output means outputs a message that the subject is in a potentially serious condition.

16. The body water meter according to claim 15, further comprising:
reception means for receiving an identifier for use in identifying the subject; and
transmission means for transmitting the identifier received by the reception means in relation to the water amount data acquired through the measurement of the amount of water in the subject's body.

17. The terminal according to claim 7, wherein the other data is body temperature data acquired through measurement of a body temperature of the subject, and, wherein, when the water amount data is equal to or less than a first preset value, the direction means directs the search for the body temperature data.

18. The terminal according to claim 17, wherein the direction means directs the search for the body temperature data that had been measured within a predetermined period of time before a measurement date and time at which the water amount data was measured.

19. The terminal according to claim 18, wherein, when the water amount data is equal to or less than the first preset value and the body temperature data is equal to or more than a second preset value, the output means outputs a message that the subject is in a potentially serious condition.

20. The terminal according to claim 19, further comprising:
- reception means for receiving an identifier for use in identifying the subject; and
- transmission means for transmitting the identifier received by the reception means in relation to the water amount data acquired through the measurement of the amount of water in the subject's body.

* * * * *